United States Patent
Saint Gal de Pons

(10) Patent No.: US 6,309,599 B1
(45) Date of Patent: Oct. 30, 2001

(54) APPARATUS FOR DETERMINING THE CONTENT OF A PREDETERMINED SUBSTANCE IN A FLUID

(75) Inventor: Renaud Saint Gal de Pons, Nimes (FR)

(73) Assignee: Metrologie et Systemes Industriels de Regulation (M.E.S.I.R. S.A.), Nimes (FR)

( * ) Notice: Subject to any disclaimer, the term of this patent is extended or adjusted under 35 U.S.C. 154(b) by 0 days.

(21) Appl. No.: 09/125,125

(22) PCT Filed: Feb. 14, 1997

(86) PCT No.: PCT/FR97/00286

§ 371 Date: Aug. 11, 1998

§ 102(e) Date: Aug. 11, 1998

(87) PCT Pub. No.: WO97/31261

PCT Pub. Date: Aug. 28, 1997

(30) Foreign Application Priority Data

Feb. 20, 1996 (FR) .................................................. 96 02083

(51) Int. Cl.⁷ ........................... G01N 31/22; G01N 25/20; G01N 33/497

(52) U.S. Cl. .................................. 422/59; 422/84; 422/85; 436/132; 436/147; 73/23.3

(58) Field of Search .................................. 422/59, 84, 85, 422/58, 60; 436/132, 147, 148; 73/23.3

(56) References Cited

U.S. PATENT DOCUMENTS

| | | | |
|---|---|---|---|
| 3,459,508 | * 8/1969 | Miczka | 436/89 |
| 3,823,382 | * 7/1974 | Gaddy | 180/272 |
| 4,300,385 | 11/1981 | Albarda . | |
| 4,354,854 | 10/1982 | Fritze et al. . | |
| 4,791,065 | * 12/1988 | Rislove | 436/132 |
| 5,171,535 | 12/1992 | Lamont . | |

FOREIGN PATENT DOCUMENTS

| 43042 | 1/1982 | (EP) . |
|---|---|---|
| 480177 | 4/1992 | (EP) . |

* cited by examiner

Primary Examiner—Jill Warden
Assistant Examiner—LaToya I. Cross
(74) Attorney, Agent, or Firm—Duane Morris

(57) ABSTRACT

This invention relates to an apparatus for determining a given substance content of a fluid comprising a means for monitoring the fluid volume passing through the tube, and a heat sensitive indicator for indicating that the reactant mass has reached a critical heating temperature corresponding to a fluid volume flowing through the mass equal to a predetermined calibrated volume.

15 Claims, 2 Drawing Sheets

APPARATUS FOR DETERMINING THE CONTENT OF A PREDETERMINED SUBSTANCE IN A FLUID

This application is a 371 of PCT/FR97/00286, filed Feb. 14, 1997.

FIELD OF THE INVENTION

This invention relates to an apparatus for determining or metering a given substance content of a fluid.

BACKGROUND OF THE INVENTION

Such apparatuses are already known for testing the alcohol content in the exhaled breath, and estimating the alcohol content of the blood.

Among these known apparatuses for testing the percentage of alcohol, an ethylometer or Alcotest™ currently available in the market is shown on FIG. 1 of the enclosed drawings and comprises:

- a means for sensing the alcoholic vapors in the breath, comprising a porous reactant mass 1 which progressively changes color by chemical reaction with said alcoholic vapors according to the volume of gas flowing through said mass,
- a hollow tube 2 opened at its longitudinal ends, wherein said mass is housed so that the exhaled air entering the tube by one end passes through the mass and flows out by the other end,
- a means for metering the alcohol content in the breath, comprising a graduation 3 on the portion of the tube containing the reactant mass, said graduation being calibrated according to a predetermined volume of gas passing through the mass, and
- a means for limiting the gas volume passing through the tube, comprising a flexible inflatable bladder 4, intended to be connected to one end of the tube and the inflation of which is limited to the aforementioned predetermined calibrating volume, said bladder being provided with a valve at its nozzle.

The operation of this Alcotest™ consists of blowing into the limiting bladder until it is completely full, then completely emptying the bladder through the tube after inserting the nozzle 5 of the bladder onto an end of the tube, and finally comparing the graduated mark of reference 3 with the length of reactant which changed color, to obtain an evaluation of the alcohol content of the blood. However, this type of ethylometer exhibits many drawbacks, in particular risks of leakage in the limiting bladder itself and at its connection to the tube, whereas the apparatuses have no tightness deficiency. There results a great overcost to obtain such as tightness.

This apparatus is also complicated in use since it requires three separate operations for the user. On the other hand, when the test is negative, the reactant mass does not change color but reacts with the water vapor contained in the exhalation, which makes the tube unusable, namely inoperable for a subsequent use. However, nothing on the tube let's know whether it is unused or has already been used during a negative test, since the tube and the inflatable bladder are in two separated parts.

The object of this invention is therefore to overcome the aforementioned drawbacks and to provide a novel lightweight portable apparatus for determining or metering a given substance content of a fluid, which is simple to manufacture and to use.

SUMMARY OF THE INVENTION

In this respect, this invention provides an apparatus for determining a given substance content of a fluid, comprising: a means for sensing the presence of said substance in the fluid, comprising a porous reactant mass which progressively reacts with said substance according to the fluid volume flowing through the mass, said porous mass being generally selected so that it turns color during the chemical reaction with the substance,

- a hollow tube opened at its two longitudinal ends, wherein said mass is housed,
- a means for determining the substance content of the fluid, comprising for instance a graduated metering means on the longitudinal portion of the tube containing the reactant mass, said means being calibrated according to a predetermined fluid volume flowing through the mass,
- wherein it comprises a means for monitoring the fluid volume passing through the tube, comprising a heat sensitive indicator for indicating that the reactant mass has reached a critical heating temperature corresponding to a fluid volume flowing through the mass equal to the aforementioned predetermined calibrating volume did pass through the tube and hence that the user must stop blowing.

The invention is therefore based on the use of the exothermic reaction between the reactant mass and the fluid and onto the correlation between the fluid volume passing through the mass and the heating temperature thereof.

In a first preferred embodiment of the invention, the aforementioned heat indicator comprises a reactant solution such as an ink which instantaneously turns color and in a non reversible way when said critical temperature is reached. In an alternative embodiment, this reactant solution is absorbed into a chip which is secured to or embedded into the inner or outer walls of the tube, at the vicinity or at the level of said reactant mass.

According to another inventive feature, the indicator is arranged on the tube periphery at the level of the porous reactant mass and in a determined position for serving at the same time as a reference mark for determining the substance content of the fluid. The heat indicator may be carried by a removable ring for a reuse of the indicator onto another tube, when the heat indicator could be dissociated from the reference mark and positioned at the downstream end of the reactant mass.

In another embodiment, said heat indicator comprises an acoustic alarm or a light signal which is activated when the critical temperature is reached.

Still in another embodiment, said heat (thermal) indicator comprises a temperature sensor and a means for displaying the sensed temperature.

According to another inventive feature, the apparatus comprises an element for indicating the apparatus's used or unused state, said indicating element consisting of a non reversible heat indicator.

Indeed, even when the test is negative, the exothermic reaction is produced and therefore activates the heat sensitive indicator which indicates that the apparatus has already been used.

According to still another inventive feature, the apparatus comprises an element for indicating the apparatus's out of date or in date state, said indicating element consisting of a non reversible heat sensitive indicator, and the critical temperature of which is set at the temperature at which the reactant mass is likely to degrade by the action of an external heating, for instance by an extended exposure of the apparatus under the sun.

The critical temperature is advantageously selected in the range of 45° C. to 70° C., wherein the heating curve of the exothermic reaction with respect to the fluid volume hardly varies with the ambient temperature. Preferably, the critical temperature is substantially equal to 55° C.

The inventive apparatus may be used for instance as alcotest or for metering the pollution rate of nitrogen monoxide, nitric vapor or carbon dioxide in air, or still for metering a given substance rate in a liquid.

BRIEF DESCRIPTION OF THE DRAWINGS

The invention will be better understood and other objects, details, features and advantages thereof will more clearly come from the following explanatory description of several particular presently preferred embodiments of the invention, given for an illustrative and non limitative scope only, by referring to the enclosed diagrammatical drawings wherein.

DETAILED DESCRIPTION OF THE INVENTION

Figure 1:
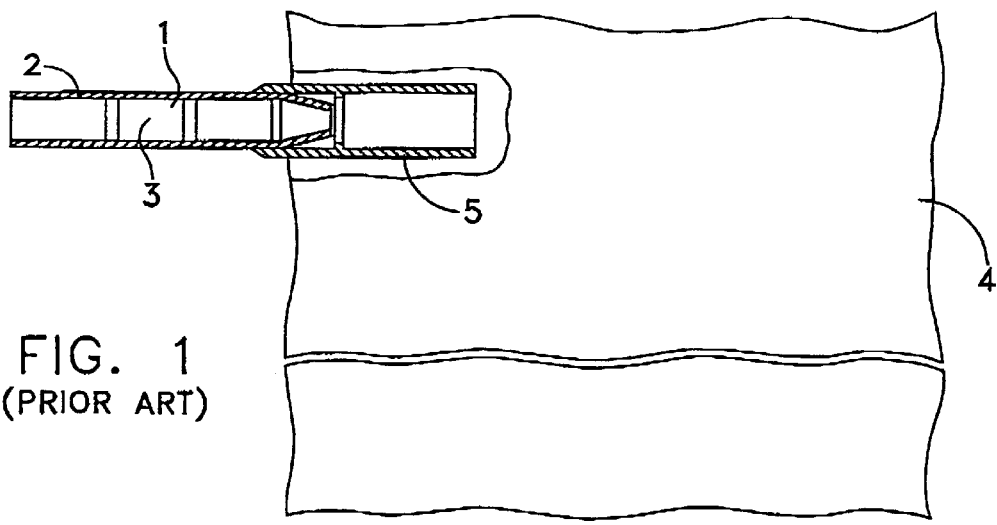
FIG. 1 is a diagrammatical partial view in partial section of a known ethylotest.
Figure 2:
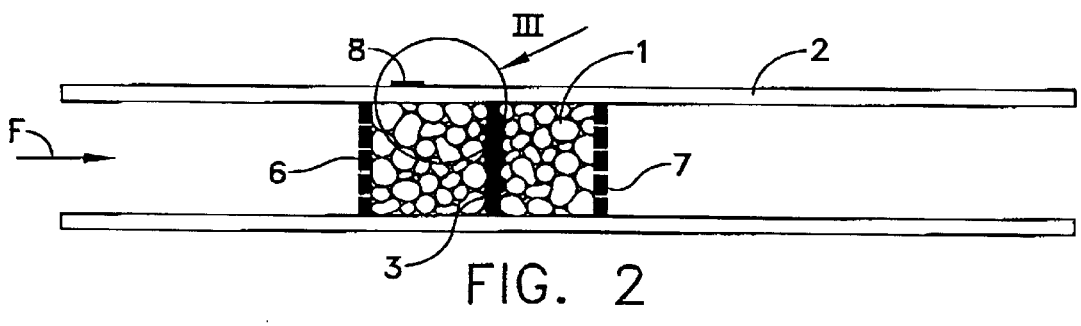
FIG. 2 is a diagrammatical view of a first embodiment of the invention.
Figure 3:
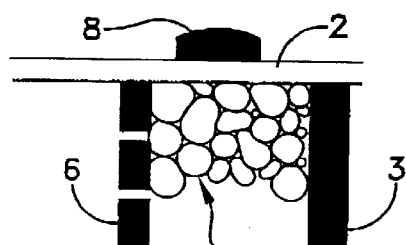
FIG. 3 is a partial view showing a detail of FIG. 2, indicated by the arrow III.

According to the exemplary embodiment shown in FIGS. 2 and 3, the inventive apparatus comprises a porous reactant mass 1 comprising for instance a chromium VI salt carried by silica granulates, and a hollow tube 2 having open end in which is secured the granulates constituting said mass.

Two screens or perforated partitions 6, 7 are transversely secured within the tube 2 on both sides of the mass 1, for holding the granulates constituting said mass.

These screens 6, 7 may also serve for filtering and regulating the fluid flow passing through the mass 1.

There is shown in FIG. 2 a graduation comprising one reference mark 3 only corresponding to the maximum alcohol rate authorized by the law, but it is of course possible to graduate the tube throughout the length of its reactant mass containing portion.

One may also substitute the graduation by another means for determining the alcoholic rate, comprising a reference luminance of the color change for the reactant mass carried for instance on the tube, the substance content being determined by reading the contrast between said reference luminance and the actual luminance of the color change.

There is shown in FIGS. 2 and 3 that a chip 8 is glued on the outer face of the tube walling 2, at the level of the reactant mass 1, and more precisely between the upstream screen 6 and the reference mark 3.

This chip 8 contains an ink, a paint or a heat sensitive filler which instantaneously changes color and in a non reversible way when a given critical temperature has been reached.

Such an ink, paint or filler is known per se and is used in particular onto the packaging of deep-frozen products for controlling that their temperature is kept into the authorized preservation ranges.

The porous reactant mass is also known per se and may be prepared by any convenient process.

Figure 4:
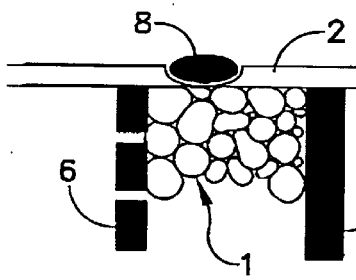
FIG. 4 to 7 are views similar to FIG. 3, but showing alternative embodiments of the invention.
Figure 5:
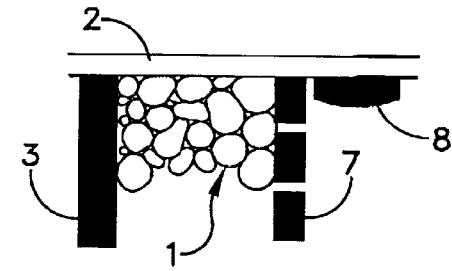

In the alternative embodiment shown in FIG. 4, the chip 8 is embedded onto the outer face of the tube walling 2. In FIG. 5, the chip 8 is glued onto the inner face of the tube walling 2 in the vicinity of the aforementioned downstream screen 7.

Figure 6:
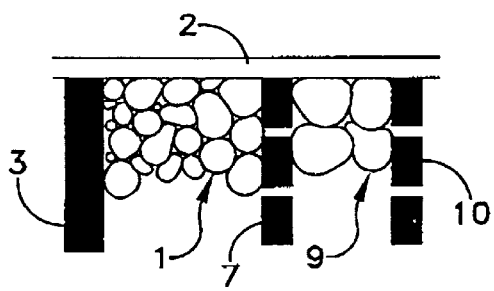

In the embodiment of FIG. 6, the chip 8 is removed and substituted by additional silica granulates 9 impregnated with said ink, said granulates 9 being housed into the tube 2 and maintained between the downstream screen 7 and another similar screen 10.

Figure 7:
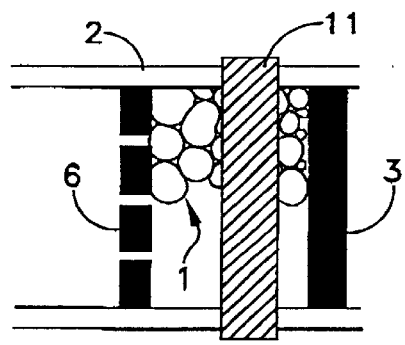

In another embodiment shown on FIG. 7, the inventive apparatus comprises a peripheral ring 11 which externally encircles the tube 2, at the level of the reactant mass 1, more precisely between the upstream screen 6 and the downstream screen 7 at a position corresponding to the aforementioned reference mark 3, for serving as a graduation of the metering means.

The ring 11 holds the heat sensitive indicator indicating when the reactant mass 1 reaches the aforementioned critical temperature, and may be removable for its reuse when the indicator is reversible.

Figure 8:
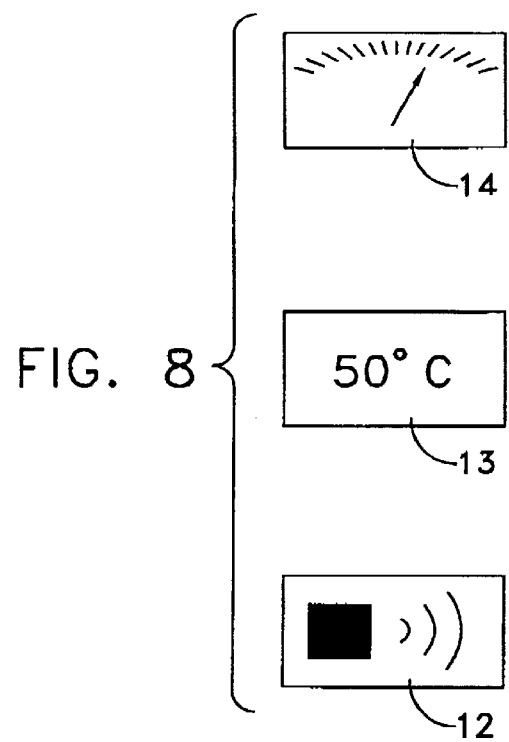
FIG. 8 diagrammatically shows three other heat sensitive indicators which may be used in the inventive apparatus.

There is shown in FIG. 8, a first indicator comprising an acoustic alarm 12 which is activated when the critical temperature is reached, for instance by a fuse or a differential dilatation bimetal system, a second indicator comprising a digital temperature display 13, and a third indicator comprising a needle graduated temperature display 14, the last two indicators 13, 14 being connected to a not shown temperature sensor.

One may also provide instead of the acoustic alarm 12 a light signal.

Figure 9:
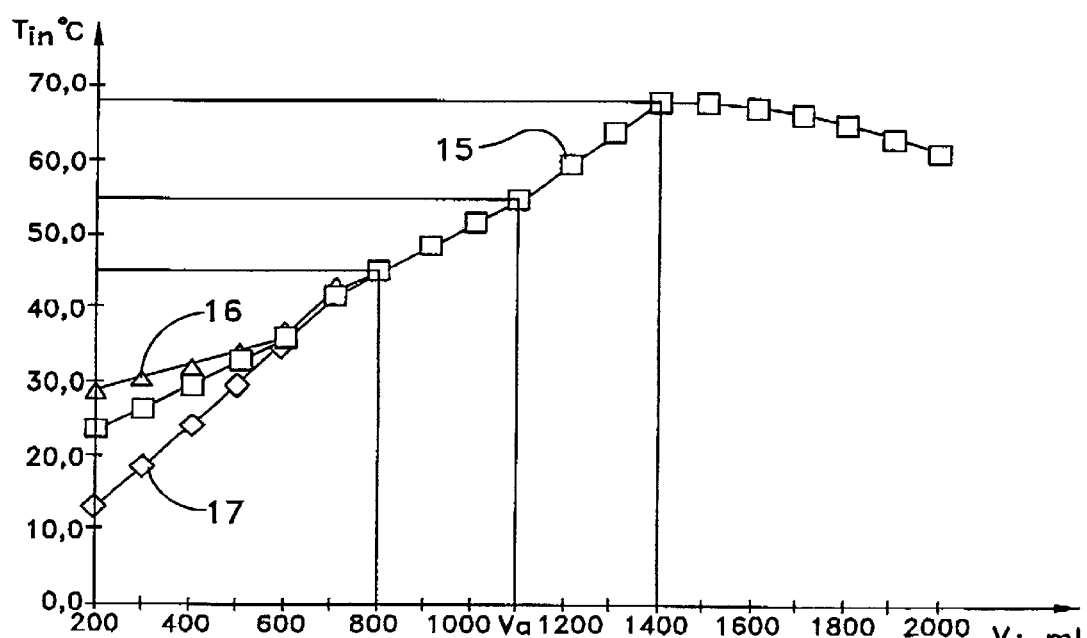
FIG. 9 is a graph showing the heating curve of the reactant mass with respect to the fluid volume passing therethrough.

A particular use of the invention will be now described by referring to the graph shown in FIG. 9.

This graph shows the evolution of the temperature curve of a porous reactant mass with respect to the gas volume passing therethrough.

In this particular application, the porous reactant mass comprises a silica gel impregnated with a reactant solution consisting of chromium VI salt the density of which is 1.80, and the gas is blown air at the pressure of about 30 millibars.

The temperature generated by the exothermic reaction between the water vapor contained in the gas and the chemical reactant carried by the silica gel has been measured according to the volume of gas blown through three samples of this porous reactant mass.

The mean values over the three samples of the measured temperature are indicated in the Table here below according to the air volume.

TABLE

| Mean Temperature in ° C. | Air Volume in ml |
|---|---|
| 20.0 | 0 |
| 21.7 | 100 |
| 23.3 | 200 |
| 26.0 | 300 |
| 30.7 | 400 |
| 33.7 | 500 |

TABLE-continued

| Mean Temperature in ° C. | Air Volume in ml |
|---|---|
| 36.3 | 600 |
| 41.0 | 700 |
| 44.3 | 800 |
| 47.7 | 900 |
| 51.0 | 1000 |
| 54.7 | 1100 |
| 59.0 | 1200 |

It should be noted here that the temperature values indicated in this Table have been measured by a temperature sensor spaced apart from the porous reactant mass by a thin plastic partition, so that these values therefore integrate the thermal inertia of a plastic tube walling. of course, the tube walling could be in a different material, for instance glass.

The mean temperature values indicated in this Table deviate from the temperature measured for each sample by only ±1° C. to 2° C.

The measures indicated in the above Table have been obtained for an ambient temperature of 20.0° C. and are shown on the graph of FIG. 9 by the square points curve 15. On the graph of FIG. 9, is also shown a triangular points curve 16 representing the measures carried out at an ambient temperature lower than 20° C.

One may see on FIG. 9 that the three curves 15, 16 and 17 merge into each other from a fluid volume higher than about 70° C. for a volume of 1400 ml before decreasing thereafter. Consequently, the operable range of temperature whatever the ambient temperature be, for selecting the critical temperature Tc of the thermosensitive indicator, is between about 45° C. and 70° C. which defines a calibrating volume Vo between around 800 and 1400 ml.

A critical temperature Tc is for instance selected equal to 55° C., at which defines a calibrating volume Vo equal to about 1100 ml. Then the tube graduation will be carried out for a gas volume passing through the tube equal to Vo.

Figure 10:
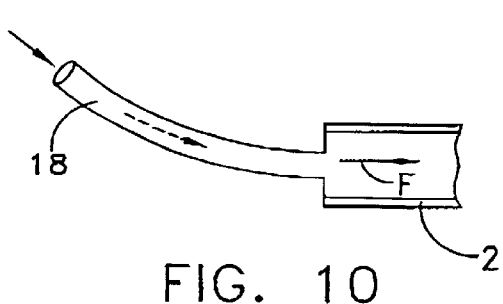
FIG. 10 is a partial view of still another embodiment of the inventive apparatus.

On FIG. 10, there is shown a flexible nozzle or tip shaped as a plastic tube 18 secured to the upstream end of the tube 2 to enable a user blowing through the tube to see the heat indicator 8 and to stop blowing as soon as possible the heat reactant changes color, since then a gas volume Vo would have been blown through the mass 1.

The operation of the inventive apparatus will be now briefly described by reference to FIG. 2.

The user directly blows through the tube 2, following the arrow F indicated in FIG. 2, without using any bladder.

During the blowing, the water vapor contained in the blown gas undergoes an exothermic reaction with the chemical reactant when it passes through the mass 1, which produces a progressive heating thereof.

When the heat generated by this exothermic reaction reaches the predefined critical temperature Tc for the thermal indicator 8, the latter changes color and the user immediately refrains from blowing since an air volume Vo would have been passed through the mass 1.

The user may then check whether the chemical reactant contained in the mass 1 has changed color on a length extending beyond the reference mark 3.

If the thermal indicator 8 is of a non reversible color change type, the user would know that this tube is now used, even though the reactant mass has not changed color because its breath did not contain any trace of alcoholic vapor. On the other hand, if the user leaves an unused tube in its vehicle which remains under extended sun exposure, and that this tube consequently rests into a heat extending beyond 55°, the heat indicator 8 would change color, which indicates to the user that the tube is out of date because of the heat degradation of the chemical reactant.

Although the invention has been described by reference to particular embodiments, it is obvious that it is by no way limited thereto and that it comprises all the technical equivalents to the described means as well as their combinations if they fall within the scope of the annexed claims.

What is claimed is:

1. Apparatus for determining a given substance content of a fluid, comprising:
    means for sensing the presence of said substance in the fluid, comprising a porous reactant mass which progressively reacts with said substance by changing color during the reaction, according to the substance content volume flowing through the mass,
    an open ended hollow tube that houses said mass,
    means for determining the substance content of the fluid said means for determining being calibrated according to a predetermined substance content volume flowing through the mass, and
    means for monitoring the substance content volume passing through the tube, comprising a heat sensitive indicator for indicating that the reactant mass has reached a critical temperature corresponding to a substance content volume flowing through the mass equal to said predetermined calibrated substance content volume, wherein said heat sensitive indicator comprises a reactant solution which turns color when said critical temperature is reached, wherein the heat sensitive indicator is secured to the tube walling at the level of the porous reactant mass and in a determined position for serving at the same time as a reference mark for determining the substance content of the fluid.

2. Apparatus according to claim 1, wherein said reactant solution is absorbed into silica granulates held within the tube in the vicinity of the reactant mass.

3. Apparatus according to claim 1, wherein said reactant solution is absorbed into a chip which is secured to the tube walling, on an inner face of said chip at the level of said reactant mass.

4. Apparatus according to claim 1, wherein said heat sensitive indicator comprises an acoustic alarm or a light signal which is activated when the critical temperature is reached.

5. Apparatus according to claim 1, wherein said heat sensitive indicator comprises a temperature sensor and means for displaying a sensed temperature.

6. Apparatus according to claim 1, wherein said heat sensitive indicator comprises a reversible heat sensitive indicator that is attached to a removable ring for a reuse of the heat sensitive indicator on another tube.

7. Apparatus according to claim 1, further comprising means for indicating a state of use, said means for indicating comprising a nonreversible heat sensitive indicator.

8. Apparatus according to claim 1, further comprising means for indicating an out of date state, said means for indicating comprising a nonreversible heat sensitive indicator wherein the critical temperature of said heat sensitive indicator is set at the temperature at which the reactant mass is likely to degrade by reaction of an external heating.

9. Apparatus according to any of the foregoing claims, wherein the critical temperature is in the range of 45° C. to 70° C.

10. Apparatus according to claim 8, wherein the critical temperature is substantially equal to 55° C.

11. Apparatus according to claim 9, wherein the critical temperature is substantially equal to 55° C.

12. Apparatus according to claim 1, wherein said reactant solution comprises an ink.

13. Apparatus according to claim 1, wherein said means for determining the substance content of said fluid comprises a graduated metering means on said tube.

14. Apparatus according to claim 3, wherein said chip is embedded into said tube wall.

15. Apparatus according to claim 3, wherein said reactant solution is absorbed into a chip which is positioned on said tube wall on an outer face of said chip.

* * * * *